United States Patent [19]
Selby et al.

[11] Patent Number: 5,667,302
[45] Date of Patent: Sep. 16, 1997

[54] SELECTIVE VOLATILIZATION AND COLLECTION

[75] Inventors: Theodore W. Selby, Midland; Brian J. Cluff, Bay City, both of Mich.

[73] Assignee: Tannas Co., Midland, Mich.

[21] Appl. No.: 577,964

[22] Filed: Dec. 26, 1995

Related U.S. Application Data

[63] Continuation-in-part of Ser. No. 517,429, Aug. 21, 1995, which is a continuation-in-part of Ser. No. 425,588, Apr. 20, 1995.

[51] Int. Cl.$^6$ .................................................. G01N 25/56
[52] U.S. Cl. ............................................................. 374/54
[58] Field of Search ................................ 374/54; 422/101, 422/105, 109, 129

[56] References Cited

U.S. PATENT DOCUMENTS

| | | |
|---|---|---|
| 1,917,637 | 7/1933 | Dwyer . |
| 2,116,442 | 5/1938 | McLuer .......................... 422/101 X |
| 3,484,077 | 12/1969 | Porter ............................. 422/103 X |
| 5,242,643 | 9/1993 | Kim et al. ............................. 422/129 |

OTHER PUBLICATIONS

JPI-55-41-93 (1993).
CEC-L-40-T-87 (1987).
Ace Glass, Inc., Catalog, 1200, 1992, pp. 281-284, 353 & 382.
Cole-Parmer Instrument Co., 1993-1994 Catalog, pp. 414-415.
Hydrick, *Lubricants World*, 4:12, Dec. 1994, pp. 7, 10-11 & 14.
Roberts et al., "An Introduction to Modern Experimental Organic Chemistry," 2nd Ed., Holt, Rinehart and Winston, Inc., New York, 1974, p. 36 & back plate.
Rudy, "Cobalt (III) Complexes with (R)-1,2-Diaminopropane and Its Derivatives," W. Mich. U., M.A., 1985, University Microfilms, Ann Arbor, Mich., pp. 32-33.
Schloemann, "Modified Noack Volatility Studies," Savant, Inc. Dec. 6, 1994.
Selby, "The Problems and the Opportunities in the Use and Reuse of Lubricating Oils to Meet the Needs of Modern Engines," 1994.
Selby et al., "A New Approach to the Noack Volatility Test," Jan. 11–13, 1994.
Selby et al., "Base Oil Characterization Techniques Using a New Approach to the Noack Volatility Test," 1994.
Selby et al., "Engine Oil Volatility Studies–Generation of Phosphorus," 1995.

*Primary Examiner*—George M. Dombroske
*Assistant Examiner*—Paul D. Amrozowicz
*Attorney, Agent, or Firm*—Christopher John Rudy

[57] ABSTRACT

Selective volatilization and collection method includes providing a substance, for example, solid and/or liquid, in a contained system; providing thermal energy to the system and substance, and a current, i.e., directed mass flow, from external to the system, such that, substantially without boiling, nor disturbing the substance surface, at least one component of the substance is volatilized. Volatilized substance component(s) are gently swept away from remaining substance by the current and collected. Apparatus useful in the method includes a generally enclosed vessel for holding the substance; gaseous matter entry port, with its exit end above the substance; and exit/collection port with a feature for collection of volatilized substance. An entry port wand having a throttle, porous ball, director channel(s) or other feature for tempering and/or directing incoming gaseous matter, which supplies the current in the method, may be in the apparatus.

12 Claims, 1 Drawing Sheet

SELECTIVE VOLATILIZATION AND COLLECTION

CROSS-REFERENCE

This is a continuation-in-part of application Ser. No. 08/517,429 filed Aug. 21,1995 which is a continuation-in-part of application Ser. No. 08/425,588 filed Apr. 20,1995. The same are incorporated herein by reference.

FIELD

In general, this invention concerns a method useful for volatilization of a substance such as from a liquid and/or a solid and collection of the vapor produced. An apparatus which is useful in the method may also be of concern.

BACKGROUND

In previous disclosures, Selby et al., Ser. No. 08/425,588, and Selby, Ser. No. 08/517,429, described a fluid coalescing method and apparatus, and vapor removal. Although these disclosures constitute significant advances in the art, room exists for further improvements.

SUMMARY

Following upon serious, dedicated inquisition and research into the matter, the present invention has been discovered and developed. It provides, in one aspect, a method for selective volatilization and collection of a substance, which comprises providing a substance in a coalesced state, the substance having a surface boundary in contact with matter provided in the gaseous state, said provided substance and matter being substantially contained in a system for at least a portion of time the same are provided; providing thermal energy to the system including to the substance, and providing a current within the matter in the gaseous state, the current having an origin external to the system, such that, substantially without boiling being observable by the naked eye and without substantially disturbing the surface boundary of the substance, at least one component of the substance becomes volatilized and crosses the surface boundary into the matter provided in the gaseous state; gently sweeping the volatilized substance component(s) in the matter in the gaseous state away from the boundary of remaining substance and the matter; and collecting the volatilized substance component(s). In another aspect, in general, an apparatus which is useful with the method can comprise a generally enclosed vessel capable of holding the substance, a gaseous matter entry port such that its exit end, for providing the gaseous matter to the interior of the vessel, is disposed above the boundary of the substance, and an exit/collection port with means for collection of the volatilized component(s) of the substance. An entry port wand with a throttle and/or porous ball or director channel(s), or other means of tempering and/or directing the incoming gaseous matter, may be provided with the apparatus.

The invention is useful in analyses, separation and purification of substances.

Significantly, by the invention, analyses, particularly with multiple-component substances especially to include oil samples, are greatly improved in accuracy and precision. As well, separation and purification of substances are greatly enhanced. With preferred means for collection, collection can be highly efficient, with near total collection of oil sample components, for example, being attainable.

Numerous further advantages attend the invention.

DRAWINGS

The drawings form part of the specification hereof. In the drawings, the following is noted:

FIG. 1 of the present improvements depicts an apparatus of the invention with a throttle and porous ball containing wand.

ILLUSTRATIVE DETAIL

Figure 1:
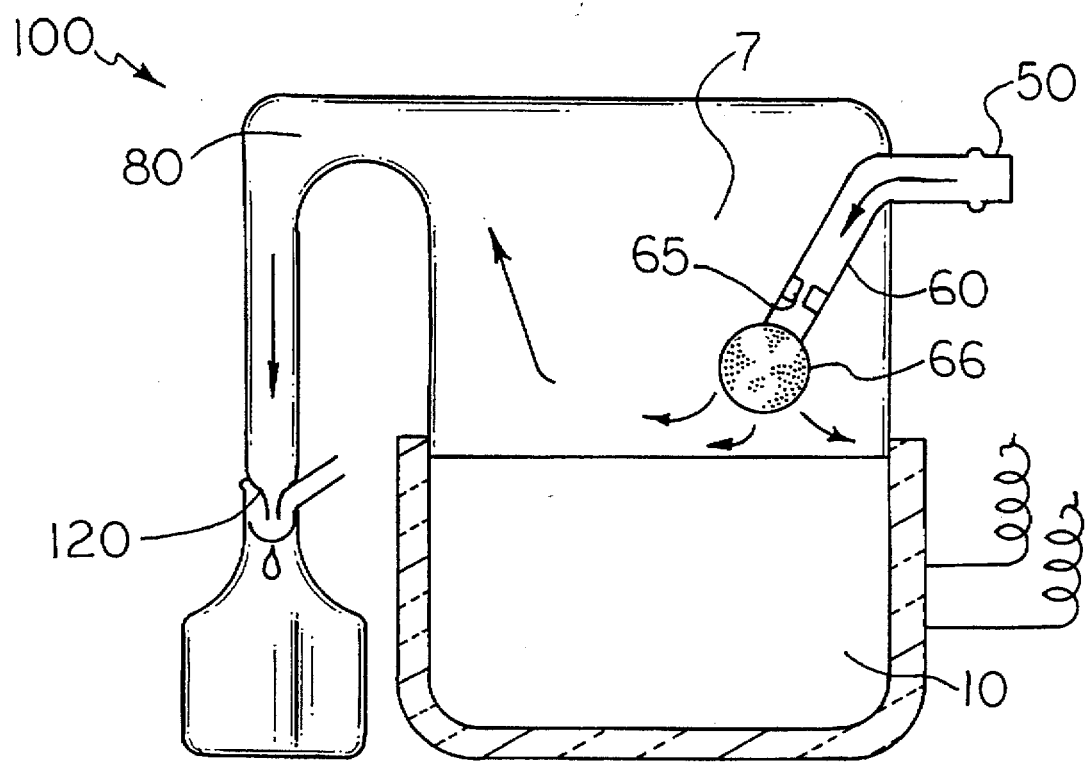

The invention can be further understood from the present detail, taken in view of the accompanying drawings and the incorporated matter. The same generally is to be construed as illustrative and not necessarily limiting in nature.

In the method for selective volatilization and collection of a substance, a substance in a coalesced state is provided. For example, the substance may be in the solid and/or liquid state, with the liquid state a preferred state. The substance may be a mixture of a plurality of components. Often, the substance is oleaginous. The substance has a surface boundary in contact with matter provided in the gaseous state. The matter may be, for example, air, nitrogen, argon, helium, hydrogen, oxygen, carbon dioxide, methane, ethane, propane, and so forth and the like, to include mixtures thereof. Air is a preferred embodiment of the matter. The provided substance and matter are substantially contained in a system for at least a portion of time the same are provided.

In the practice of the invention, thermal energy is provided to the system, including to the substance, and a directed mass flow, which may be referred to herein as "current," within the matter in the gaseous state is also provided. The thermal energy can be provided by a heating coil, an external flame, immersion of the substance contained in a vessel in a hot liquid or other heat conducting, thermally energized material, and so forth. A noble metal resistive heater, heated with the provision of electricity thereto, closely surrounding the vessel is a preferred embodiment. See e.g., Selby et al. The current has an origin external to the system. In operation, substantially without boiling being observable by the naked eye and without substantially disturbing the surface boundary of the substance, at least one component of the substance becomes volatilized and crosses the surface boundary into the matter provided in the gaseous state. One component, or set of components, at a time may so be volatilized and cross the boundary. Gentle sweeping of the volatilized substance component(s) in the matter in the gaseous state away from the boundary of remaining substance and the matter is carried out. See e.g., Selby. Nevertheless, again, the surface is generally not disturbed significantly as observed by the naked eye.

A pressure differential is generally employed in relation to the pressures inside and outside the contained system, or vessel. The pressure differential employed may be such that pressure inside the contained system is less than that which is outside the contained system. For instance, a pressure differential may be employed such that pressure inside the contained system is less than atmospheric and that which is outside the contained system is greater than that which is inside the system, to include, especially in the case of the gaseous matter being air or a gas which pressure is controlled by air pressure, the pressure inside the contained system often being less than atmospheric and that which is outside the contained system being at ambient atmospheric pressure.

The volatilized substance component(s) is/are collected. The collection may be by standard methods. However, it is preferred that collection be carried out with the collection apparatus of Selby et al. A preferred arrangement for laboratory collection, especially of engine oil or transmission fluid components is a needle valve arrangement. See e.g., Selby et al., and Selby.

The method can be continuous. It also may collect substance components in series.

Apparatus useful with the method can comprise a generally enclosed vessel capable of holding the substance, a gaseous matter entry port disposed above the boundary of the substance, and an exit/collection port with means for collection of the volatilized component(s) of the substance.

In reference to present FIG. 1, walled vessel 100 has entry port 50 with an exit flow therefrom into upper chamber 7 being above upper boundary of substance 10. Wand 60 may have throttle 65 and/or porous bulb 66 to assist in controlling and gently dispersing matter in the gaseous state into the interior of the vessel 100 above the boundary of the substance 10 therein. Dimensions of the throttle 65 and the passageway it produces can include a reducing section diameter and length in the case of tubular channels, or irregularly shaped channels of variable width, height and length. The throttle may be varied such as by selecting appropriate dimensions of the width, height and length of the channel. For instance, the throttle 65 may be generally tubular with a 0.046-inch diameter and a 0.5-inch length. The bulb 66 may be made of any suitable material such as pumice, alumina to include fused crystalline alumina grain, metal to include sintered porous stainless steel, and so forth and the like. Exit port 80 is provided, and means for collection may include pinched throughfare(s) 120 and so forth.

The invention is particularly useful in laboratory testing. It proves to be, for example, eminently adapted for replacement of old-fashioned Noack test apparatus and methodology, being more accurate and precise in operation, and more environmentally sound and operator friendly.

Accordingly, the invention may be considered to be generally described as follows:

It can employ a carrier gas stream.

Conventional condensing techniques are not necessary.

It can be a process of selectively volatilizing molecules at a non-agitated surface and collecting these molecules. Herding and gathering of the molecules are useful metaphors.

A focus can be on the collection of the molecules in a selected way. They may be herded and put in a chute for recovery.

One valve may regulate the rate of gathering and the kind of gathering. This is elaborated upon as follows: First of all, in general, it may be considered that the valve 120 sets the level of vacuum or pressure in the chamber and thus the flow through rate of carrier gas through the entry port 50, throttle 65 and exit port 80. The flow through the throttle 65 is dependent upon the pressure differential inside and outside the vessel, which differential, again, can be considered to be generally set and regulated by the valve 120 which may also be considered to be a primary throttle. Thus, a series of throttles 65 & 120 may be considered to be employed. The throttle 65, which may be of fixed dimensions, or be adjustable, i.e., variable, as desired, may be considered thus to be a secondary throttle. Moreover, the throttle, or modulating, effect can be further provided by a porous ball 66 of appropriate air resistance and/or a constriction beyond the valve 120. In view of such considerations as these, depending upon the type of substance and carrier gas provided, the carrier gas can pick up and carry away the volatilized substance, which, depending on the system, to include temperature and pressure, is generally an intensive, but often differentially changeable, property within the system.

Figure 2:
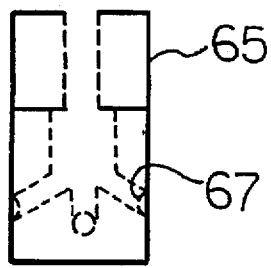
FIG. 2 depicts another embodiment of a throttle, in a side, cut-away view.
Figure 3:
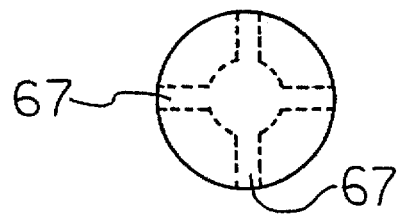
FIG. 3 depicts a top, cut-away view of the throttle of FIG. 2.

The throttle 65 and/or ball 66 may be considered to be a director of the entry gas. Further, a throttle 65, instead of a porous ball 66, for example, as depicted within FIG. 1, may be operated without the ball 66, or it may be further equipped with one or more director channels 67, for example, as depicted in FIGS. 2 & 3. For an illustration, such channels 67 may be four in number and be provided in a tetrahedrally-shaped arrangement, at a 30-degree angle downward to the general direction of flow through the throttle 65, with each individual channel 67 having a 0.046-inch or so diameter.

There is no appreciable amount of vapor below the boundary of the substance, e.g., the surface of a liquid, i.e., no boiling. Thus, control is kept of surface area.

Molecules breaking through the boundary are not necessarily the smallest molecules, etc. A different distribution of molecules from that which can be obtained with boiling may be provided.

The boundary, nevertheless, need not necessarily be a smooth surface. The method may be applicable, for example, in the crankcase of an automotive engine.

A mixture of solid and liquid components may be used.

The invention is, again, particularly well adapted for a test - which is, significantly, repeatable.

Generally, equilibrium of the substance is disturbed.

The system environment can be highly controlled.

CONCLUSION

The present invention is thus provided. Numerous adaptations can be effected within its spirit, the literal claim scope of which is particularly pointed out as follows:

We claim:

1. A method for selective volatilization and collection of an oleaginous substance, which comprises providing an oleaginous substance in a coalsaced state, the coalesced, provided substance having a surface boundary in contact with matter provided in the gaseous state, said provided substance and matter being substantially contained in a system for at least a portion of time the same are provided; providing thermal energy to the system including to the coalsaced, provided substance, and providing a current within the matter in the gaseous state, the current having an origin external to the system, such that, substantially without boiling being observable by the naked eye in, and without substantially disturbing the surface boundary of, the coalesced, provided substance thereby, at least one component of the coalesced, provided substance becomes volatilized and crosses the surface boundary into the matter provided in the gaseous state; gently sweeping the volatilized substance component(s) in the matter in the gaseous state away from the boundary of remaining coalsaced, provided substance and the matter, without substantially disturbing the surface boundary of the remaining coalsaced, provided substance thereby; and collecting the volatilized substance component(s).

2. The method of claim 1, wherein the matter provided in the gaseous state is ambient air.

3. The method of claim 1, wherein a pressure differential is employed such that pressure inside the contained system is less than that which is outside the contained system.

4. The method of claim 2, wherein a pressure differential is employed such that pressure inside the contained system is less than atmospheric and that which is outside the contained system is at ambient atmospheric pressure.

5. An apparatus useful in a method for selective volatilization and collection of an oleaginous substance, which method includes providing an oleaginous substance in a coalsaced state, the coalsaced, provided substance having a surface boundary in contact with matter provided in the gaseous state, said provided substance and matter being substantially contained in a system for at energy to the system including to the coalesced, provided substance, and providing a current within the matter in the gaseous state, the current having an origin external to the system, such that, substantially without boiling being observable by the naked eye in, and without substantially disturbing the surface boundary of, the coalesced, provided substance thereby, at least one component of the coalesced, provided substance becomes volatilized and crosses the surface boundary into the matter provided in the gaseous state; gently sweeping the volatilized substance component(s) in the matter in the gaseous state away from the boundary of remaining coalesced, provided substance and the matters, without substantially disturbing the surface boundary of the remaining coalesced, provided substance thereby; and collecting the volatilized substance component(s), which apparatus comprises a generally enclosed vessel having walls and which form an interior chamber with lower and upper regions, which vessel is capable of holding the coalsaced, provided substance in the lower region; disposed through a wall of the vessel, a gaseous matter entry port having an entry and exit end, with an entry port wand between the entry end exit ends to provide a passageway for the gaseous matter therebetween, such that its exit end, which exit end is for providing the gaseous matter to the interior of the vessel, above the boundary that the oleaginous, provided substance has with the matter in the gaseous state, which exit end is in the upper region of the vessel chamber and which exit end can be disposed above said boundary and is in the upper region of the vessel chamber; and, disposed through a wall of the vessel to the upper region of the vessel chamber, an exit/collection port with means for collection of the voletilized component(s) of the substance, wherein the entry port wand has a throttle and at lease one of the porous ball and director channel (s) therewith to assist in controlling and gently dispersing the matter in the gaseous state into the upper interior chamber of the vessel, above the boundary of the coalesced, provided substance therein—and wherein the apparatus is useful in the aforesaid method.

6. The apparatus of claim 5, wherein the entry port wand is equipped with a throttle additionally having a porous ball.

7. The apparatus of claim 5, wherein the entry port wand is equipped with a throttle additionally having a plurality of director channels.

8. A method for selective volatilization and collection of an oleaginous substance, comprising providing an oleaginous substance in a coalesced state, the coalsaced, provided substance having a surface boundary in contact with matter provided in the gaseous state, said provided substance and matter being substantially contained in a system for at least a portion of time the same are provided; providing thermal energy to the system including to the coalesced, provided substance, and providing a current within the matter in the gaseous state, the current having an origin external to the system, such that, substantially without boiling being observable by the naked eye in, and without substantially disturbing the surface boundary of, the coalesced, provided substance thereby, at least one component of the coalesced, provided substance becomes volatilized and crosses the surface boundary into the matter provided in the gaseous state; gently sweeping the volatilized substance component (s) in the matter in the gaseous state away from the boundary of remaining coalsaced, provided substance and the matter, without substantially disturbing the surface boundary of the remaining coalesced, provided substance thereby; and collecting the volatilized substance component(s), which method is carried out by employing an apparatus which embraces a generally enclosed vessel having walls and which form an interior chamber with coalesced, provided substance in the lover region; disposed through a wall of the vessel, a gaseous matter entry port having an entry and exit end, with an entry port wand between the entry end exit ends to provide a passageway for the gaseous matter therebetween, such that its exit end, which exit end is for providing the gaseous matter to the interior of the vessel, above the boundary that the oleaginous, provided substance has with the matter in the gaseous state, which exit end is in the upper region of the vessel chamber and which exit end can be disposed above said boundary and is in the upper region of the vessel chamber; and, disposed through a wall of the vessel to the upper region of the vessel chamber, an exit/collection port with means for collection of the volatilized component(s) of the substance, wherein the entry port wand has at least one of a throttle, porous ball and director channel(s) therewith to assist in controlling and gently dispersing the matter in the gaseous state into the upper interior chamber of the vessel, above the boundary of the coalesced, provided substance therein.

9. The method of claim 8, wherein the coalesced, provided substance is on engine oil.

10. The method of claim 9, wherein the current is from air.

11. The method of claim 10, which is carried out under vacuum.

12. The method of claim 8, wherein the collected substance has a different distribution of molecules from that obtained by boiling.

* * * * *